United States Patent [19]

Tanimoto et al.

[11] Patent Number: 4,731,475

[45] Date of Patent: Mar. 15, 1988

[54] METHOD FOR PREPARING SOLID P-DISODIUM HYDROXYBENZOATE

[75] Inventors: Fumio Tanimoto, Kyoto; Hisao Kitano, Ohsaka, both of Japan

[73] Assignee: Nippon Petrochemicals Co., Ltd., Japan

[21] Appl. No.: 43,323

[22] Filed: Apr. 28, 1987

[30] Foreign Application Priority Data

Apr. 30, 1986 [JP] Japan .................. 61-99597

[51] Int. Cl.$^4$ ............................................. C07C 65/01
[52] U.S. Cl. .................................................... 562/475
[58] Field of Search ......................................... 562/475

[56] References Cited

FOREIGN PATENT DOCUMENTS 237196 12/1959 Australia .............................. 562/475
186905 10/1966 U.S.S.R. ............................... 562/475

Primary Examiner—Paul J. Killos
Attorney, Agent, or Firm—Ostrolenk, Faber, Gerb & Soffen

[57] ABSTRACT

The present invention provides a method for preparing solid p-disodium hydroxybenzoate which is characterized by comprising the steps of reacting phenol, carbon tetrachloride in an amount of 0.9 to 1.2 moles per mole of phenol and sodium hydroxide in an amount of 7 to 20 moles per mole of phenol prior to the reaction in an aqueous liquid containing 10 to 40% by weight of p-disodium hydroxybenzoate and/or sodium chloride in the presence of a transition metal powder in an amount of 0.01 to 1.00% by weight based on the weight of a reaction system at a reaction temperature of 50° to 150° C.; cooling the resulting reaction mixture to a level of $-20°$ to $+20°$ C.; and separating said p-disodium hydroxybenzoate therefrom.

11 Claims, No Drawings

METHOD FOR PREPARING SOLID P-DISODIUM HYDROXYBENZOATE

BACKGROUND OF THE INVENTION

(1) Field of the Invention

The present invention relates to a novel method for preparing solid p-disodium hydroxybenzoate.

(2) Description of the Prior Art p-Hydroxybenzoic acid, which can be prepared by subjecting p-disodium hydroxybenzoate to a desodium process, has been industrially used in various fields as a raw material for polyesters, oligomer liquid crystals, medicines, sterilizers and the like.

Heretofore, p-hydroxybenzoic acid has been manufactured on an industrial scale mainly from phenol potassium and carbonic acid gas in accordance with the Kolbe-Schmitt reaction.

In this method, a yield of p-hydroxybenzoic acid is as low as about 60% at present, because of the poor recovery of potassium salts and because of the secondary production of phenol, salicylic acid and 4-hydroxyisophthalic acid.

Further, there is another method in which the Reimer-Tiemann reaction is performed by the use of phenol, carbon tetrachloride and sodium hydroxide in the presence of a copper powder (Organic Reactions, 28, p. 15, 1982), and in regard to this method, a higher yield can be expected. However, such a method as is satisfactory from an industrial and economical viewpoints has not been suggested yet. In the aforesaid method utilizing the Riemer-Tiemann reaction, a mixed phase regarding the reaction is remarkably non-uniformed. In this reaction system, there exist together various and intricate liquid and solid phases, for example, an aqueous phase, an organic oil phase, a catalyst powder and a crystal such as sodium chloride which is formed during the progress of the reaction. In addition, it is necessary to inhibit the secondary production of o-hydroxybenzoic acid. For these reasons, it is not always fair to say that the above mentioned Reimer-Tiemann method is industrially suitable for the manufacture of the solid p-hydroxybenzoic acid. With regard to the preparation of p-hydroxybenzoic acid, yield and selectivity have not been improved, and the process has not been simplified so far.

SUMMARY OF THE INVENTION

The present invention is directed to a method for preparing solid p-disodium hydroxybenzoate which is characterized by comprising the steps of reacting phenol, carbon tetrachloride in an amount of 0.9 to 1.2 moles per mole of phenol and sodium hydroxide in an amount of 7 to 20 moles per mole of phenol prior to the reaction in an aqueous liquid containing 10 to 40% by weight of p-disodium hydroxybenzoate and/or sodium chloride in the presence of a transition metal powder in an amount of 0.01 to 1.00% by weight based on the weight of a reaction system at a reaction temperature of 50° to 150° C.; cooling the resulting reaction mixture to a level of −20° to +20° C.; and separating the desired solid compound therefrom.

DESCRIPTION OF THE PREFERRED EMBODIMENTS

In the present invention, phenol, carbon tetrachloride and sodium hydroxide are reacted with one another in the presence of a transition metal powder in an amount of 0.01 to 1.00% by weight based the weight of an aqueous liquid.

Phenol may be fed to the reaction system in the form of phenol alone, a solution in which phenol is dissolved in an organic solvent such as an alcohol or a glycol, or a heated aqueous solution containing phenol. Further, phenol, when fed thereto, can take the morphology of an aqueous sodium hydroxide solution containing powdered phenol sodium (powdered sodium carbolate) or phenol sodium, i.e., a phenolate of sodium. The phenol concentration in the aqueous liquid is not particularly limited, but it is usually within the range 5 to 50% by weight, preferably 10 to 40% by weight in terms of phenol.

Carbon tetrachloride is added to the reaction system in an amount of 0.9 to 1.2 moles per mole of phenol.

Moreover, sodium hydroxide is used in the reaction in an amount of 7 to 20 moles per mole of phenol. At least a part of sodium hydroxide may be fed to the reaction system in the form of a phenolate of sodium. In this connection, it is proper that an amount of sodium hydroxide is calculated in terms of sodium.

When each of carbon tetrachloride and sodium hydroxide is employed in an amount outside the above mentioned range, the yield of p-hydroxybenzoic acid diminishes disadvantageously.

The transition metal powder is added to the aqueous solution as a catalyst in order to accelerate a dechlorination reaction or a condensation reaction of carbon tetrachloride. As such a transition metal powder, it is necessary to be relatively stable even in an alkaline reaction system and to naturally accelerate the reaction of carbon tetrachloride. Examples of the transition metals include copper, iron, reduced irons, Raney iron, Raney nickel, Raney cobalt, zinc, tin, cadmium and alloys thereof. Of these tansition metals, the industrially preferable ones are iron, copper and Raney nickel each having a rust-free fresh powder surface. The transition metal powder may be fed to the reaction system in the form of a colloid or a slurry in which the powder is suspended in water or an organic solvent. The particle diameter of the transition metal powder is not particularly limited, but the finer, the better as the catalyst. The transition metal powder is added to the reaction system in an amount of 0.01 to 1.00% by weight based on the weight of the whole reaction system. When the amount of the transition metal powder is less than 0.01% by weight, a catalytic effect of the transition metal powder is scarcely acquired, and when it is in excess of 1.00% by weight, the addition of such a large amount is not economical and is liable to unpreferably produce tar-like materials by secondary reactions. It should be noted that low-valence compounds of the above mentioned transition metals are not preferable, since they tend to react with an alkali hydroxide and lose catalytic action. The industrially preferable transition metal powder is that which has the rust-free fresh surface, as desribed above.

Phenol, carbon tetrachloride and sodium hydroxide mentioned above are allowed to react with one another with vigorous stirring in the presence of the transition metal powder in the aqueous liquid. The aqueous liquid used in the present invention means a liquid of water alone, but it may contain 30% by weight or less of an organic solvent so as to regulate the solubility of p-disodium hydroxybenzoate and to facilitate a separating operation which will be described hereinafter. Examples of the organic solvents which can be mixed with water include lower alcohols such as methanol and isopropanol; cyclic or noncyclic lower ethers such as tetrahydrofuran, dioxane and dioxthorane; lower ketones such as acetone and methyl ethyl ketone; and lower fatty acids such as formic acid and acetic acid. They are economically advantageous.

In the present invention, when phenol is reacted with carbon tetrachloride in an aqueous alkaline solution under the aforesaid conditions, p-disodium hydroxybenzoate, sodium chloride or a mixture thereof in an amount of 10 to 40% by weight based on the weight of the aqueous liquid must be present in the aqueous liquid prior to the reaction. This requirement is essential to obtain the desired solid product. p-Disodium hydroxybenzoate or sodium chloride is usually present in the state of a solution in the reaction system, but it may take another state therein, depending on concentrations of phenol and sodium hydroxide. For example, p-disodium hydroxybenzoate or sodium chloride may be present in the reaction system in the state of a powder, a colloid or a fine crystal dispersed in the aqueous liquid. In the present invention, by causing p-disodium hydroxybenzoate or sodium chloride to exist in the reaction system prior to the reaction, the polarity of the reaction system at the beginning of the reaction can be enhanced, and the specific gravity of the aqueous liquid can come close to that of carbon tetrachloride, with the result that the reaction progress smoothly, thereby heightening yield of the product. Further, in the case that the p-disodium hydroxybenzoate or sodium chloride is in the state of a dispersed powder, a convenient stirring effect can be achieved by the friction between particles of the powder and an improvement in the yield can be simultaneously expected.

However, when the total amount of p-disodium hydroxybenzoate and sodium chloride is less than 10% by weight, the yield of the solid p-disodium hydroxybenzoate is low. Inversely, when the total amount thereof is more than 40% by weight, a great deal of sodium chloride is secondarily deposited during the progress of the reaction, and the presence of sodium chloride which is a strong electrolyte additionally fosters an apparent non-uniformity of the reaction, so that unpreferably, it becomes extremely difficult to carry out the stirring operation in the reaction system.

In the present invention, a surface active agent or a solubilizing agent for the reactive materials may be further added to the reaction system in order to aid the dispersion or dissolution of the reactive materials in the aqueous liquid. The reaction system of the present invention is strongly alkaline, and specific gravities of the respective raw materials are very different from one another. Therefore, when the surface active agent or the solubilizing agent is employed, the dispersion and contact efficiency of the reactive materials can be improved, and such a function as in a interphase moving catalyst can also be expected. Since leading to an unpreferable phenomenon such as cohesion and precipitation at times, the ionic surface active agent and solubilizing agent should not be used in quantity. The proper surface active agent or solubilizing agent which is effective in the reaction system of the present invention is a nonionic polymer which can be prepared by adding an alkylene oxide such as ethylene oxide or propylene oxide to a compound having one or more hydroxyl groups such as an alcohol, phenol, an alkyl phenol, a glycol, glycerin or a saccharide. The nonionic surface active agent or solubilizing agent, when used, is added to the system in an amount of 0.1 to 5.0% by weight, preferably 0.5 to 3.0% by weight based on the weight of the aqueous solution. When the amount of the nonionic surface active agent or solubilizing agent is less than 0.1% by weight, it is impossible to obtain enough function to heighten the contact efficiency of the respective raw materials taking part in the reaction, and when it is more than 5.0% by weight, foaming occurs violently and stirring becomes difficult to carry out.

The reaction of the present invention is performed by introducing predetermined amounts of phenol, carbon tetrachloride and sodium chloride into the aqueous liquid containing a predetermined amount of p-disodium hydroxybenzoate, sodium chloride or a mixture thereof with vigorous stirring in the presence of the transition metal powder and, if necessary, the surface active agent or solubilizing agent prior to the reaction. The reaction pressure is not particularly limited, and a pressure necessary to retain an aqueous phase is enough.

In the case that an especially great deal of p-disodium hydroxybenzoate is manufactured under atmospheric pressure, carbon tetrachloride can be added to the reaction system from another outside system by means of a dropping process or a pressure pump, while the reaction is being performed.

The reaction of the present invention is performed at a temperature of 50° to 150° C., preferably 70° to 140° C. When the reaction temperature is lower than 50° C., a period of time necessary for the reaction is prolonged, which fact is uneconomical. Inversely, when it is higher than the above mentioned upper limit of 150° C., p-disodium hydroxybenzoate is decomposed and secondary reactions occur unpreferably.

A reaction time is not especially limited and is suitably selected usually within the range of 0.1 to 10 hours.

After the above reaction is over, the resulting reaction mixture is cooled to a temperature of −20° to +20° C. At this time, the desired solid p-disodium hydroxybenzoate is deposited in a crystalline or a slurry state. Accordingly, by separating the product from the reaction system, p-disodium hydroxybenzoate is prepared in the form of a solid. For this separation, there can be utilized any suitable means such as an inclination process, a filtration or a centrifugal separation. With regard to a cooling temperature, a level of −20° to +20° C. is suitable. When the cooling temperature is lower than −20° C., the reaction mixture is all solidified or slurried, so that the separating operation is hard to carry out, and when it is in excess of +20° C., the deposition of the desired product is insufficient. In both the cases, preferable results cannot be attained.

In the separated and recovered solid product, sodium chloride is contained at times in addition to p-disodium hydroxybenzoate. In order to obtain purer p-disodium hydroxybenzoate, the salt must be removed therefrom. This removal operation can be very easily carried out by a suitable separation means, for example, an extraction with the aid of an organic solvent or a recrystallization from an organic solvent.

Examples of the organic solvents used in the extraction or recrystallization include alcohols such as methanol, ethanol, isopropanol, ethylene glycol and diethylene glycol; a lower fatty acid such as acetic acid; and a non-proton organic polar solvent such as dimethylformamide.

According to the present invention, the following functional effects can be obtained:

Since p-disodium hydroxybenzoate or sodium chloride is present in the reaction system from the beginning of the reaction, the yield of p-disodium hydroxybenzoate in a solid state can be heightened. Further, after the completion of the reaction, the reaction system will not be neutralized directly, and therefore the recovery and reuse of excess sodium hydroxide can be accomplished effectively and economically.

Furthermore, by maintaining a ratio of the reactive raw materials at a constant level, the production of o-disodium hydroxybenzoate which is a by-product can be inhibited, whereby the yield of the desired p-disodium hydroxybenzoate can be improved.

Now, the present invention will be described in detail in accordance with examples, but the latter are not intended to limit the scope of the present invention.

EXAMPLE 1

Experiment 1

In a four-necked separable flask (1,000 cc) equipped with a thermometer, a reflux condenser, a stirrer and a dropping funnel were placed 20.1 g (0.21 mole) of phenol, 76.8 g (1.92 moles) of sodium hydroxide, 15.0 g of sodium chloride and 77.0 ml of water, and 0.32 g (5.0 millimoles) of a copper powder was then added thereto with vigorous stirring at 80° C. Next, 34.0 g (0.22 mole) of carbon tetrachloride was added dropwise thereto with stirring over 5 hours, while a temperature was maintained at 80° C. In the course of this operation, 0.20 g (3.1 millimole) of the copper powder was added thereto twice every 2 hours. After the completion of this addition, the reaction was additionally performed with stirring at 80° C. for 1 hour. After the reaction was over, the resultant reaction mixture was cooled to 10° C., and at this time, a crystal was deposited and was then collected by a suction filtration. Since it contained sodium chloride in addition to p-disodium hydroxybenzoate, the obtained crystalline product (23.5 g) was dissolved in 150 ml of water, and hydrochloric acid was added thereto so as to reach a faintly acidic state. The formed crystal of p-disodium hydroxybenzoate was collected, so that 18.5 g of the desired product was prepared. In consequence, the yield of solid p-disodium hydroxybenzoate was 63.8%.

Further, when hydrochloric acid was added thereto at the time of the suction filtration so as to reach a faintly acidic state, 8.0 g of p-hydroxybenzoic acid was prepared. In consequence, the total amount of p-hydroxybenzoic acid was 26.5% (yield 91.4%).

Experiment 2

The crystalline product prepared by the suction filtration in Experiment 1 was extracted with methanol, and the latter was then distilled out from the extract in order to prepare 31 g (yield 81.1%) of a p-disodium hydroxybenzoate powder.

Experiment 3

Following the same procedure as in Experiment 1, a reaction was performed except that an amount of used sodium chloride was changed from 15.0 g to 10.0 g, and methanol was then extracted out in the same manner as in Experiment 2 in order to prepare p-disodium hydroxybenzoate in a yield of 80%.

Experiment 4

Following the same procedure as in Experiment 1, a reaction was performed except that an amount of used sodium chloride was changed from 15.0 g to 5.0 g, and methanol was then extracted out in the same manner as in Experiment 2 in order to prepare p-disodium hydroxybenzoate in a yield of 62%.

Experiment 5

Following the same procedure as in Experiment 1, a reaction was performed except that an amount of used sodium hydroxide was changed from 76.8 g to 51.8 g, and methanol was then extracted out in the same manner as in Experiment 2 in order to prepare p-disodium hydroxybenzoate in a yield of 42%.

Experiment 6

Following the same procedure as in Experiment 1, a reaction was performed except that the reaction temperature was 40° C., and in this case, a total yield of p-hydroxybenzoic acid was 10%.

Experiment 7

The reaction of Experiment 1 was carried out in an autoclave at 160° C. Carbon tetrachloride and the copper powder secondly added in Experiment 1 were placed in the autoclave from the start.

A total yield of prepared p-hydroxybenzoic acid was 30%.

Experiment 8

Following the same procedure as in Experiment 1, a reaction was performed except that 10.2 g (7.7 g as an acid) of p-disodium hydroxybenzoate was substituted for 15.0 g of sodium chloride. After the completion of the reaction, suction filtration was carried out in like manner in order to recover a crystalline product. From the latter, 27.0 g of p-hydroxybenzoic acid was obtained. The filtrate was also analyzed for p-hydroxybenzoic acid, and a correction for the previously added p-disodium hydroxybenzoate was made. A total yield of obtained p-hydroxybenzoic acid was 93%.

Experiment 9

Following the same procedure as in Experiment 1, a reaction and treatment were carried out except that 15.0 g of sodium chloride was replaced with a mixture of 7.0 g of p-disodium hydroxybenzoate and 4.0 g of sodium chloride. By correcting for the added p-disodium hydroxybenzoate, it was found that p-hydroxybenoic acid was prepared in a total yield of 92.5%.

EXAMPLE 2

In each experiment in this example, phenol, sodium hydroxide, p-disodium hydroxybezoate, and sodium chloride in amounts shown in the following table and 80 ml of water were placed in a four-necked separable flask (1,000 cc) equipped with a thermometer, a reflux condenser, a stirrer and a dropping funnel. Then, 0.32 g of a copper powder was added thereto with vigorous stirring at a predetermined temperature. Next, 34.0 g (0.22 mole) of carbon tetrachloride was added dropwise thereto with stirring over 5 hours. In the course of this dropping, 0.20 g of the copper powder was added thereto twice every 2 hours. After the completion of this addition, the stirring was additionally carried out at the same temperature for 1 hour. After the reaction was over, the resultant reaction mixture was cooled to a predetermined temperature, and deposited crystalline product was collected by a suction filtration. The collected crystalline product was then extracted with ethanol, and the latter was then distilled out from the extract in order to prepare p-disodium hydroxybenzoate. Yields (%) of the obtained p-disodium hydroxybenzoate are also set forth in the following table. Needless to say, these yields are values gained by correcting for the previously added p-disodium hydroxybenzoate.

TABLE

| Experiment No. | Phenol (g) | CCl₄ (g) | p-Disodium hydroxy-benzoate (g) | NaCl (g) | NaOH (g) | Reaction Temp. (°C.) | Cooling Temp. (°C.) | Yield of p-disodium hydroxy-benzoate (%) |
|---|---|---|---|---|---|---|---|---|
| 2-1 | 20.1 | 34.0 | 10.2 | — | 76.8 | 80 | 10 | 79.0 |
| 2-2 | 20.1 | 34.0 | 10.2 | — | 76.8 | 100 | 10 | 87.0 |
| 2-3 | 20.1 | 34.0 | 5.1 | — | 79.6 | 85 | 10 | 65.0 |
| 2-4 | 20.1 | 34.0 | 56.1 | — | 76.8 | 105 | 10 | 55.0 |
| 2-5 | 20.1 | 34.0 | 10.2 | — | 54.8 | 90 | 10 | 51.0 |
| 2-6 | 20.1 | 34.0 | 10.2 | — | 76.8 | 160 | 15 | 45.7 |
| 2-7 | 20.1 | 34.0 | 10.2 | — | 80.0 | 75 | 60 | 47.5 |
| 2-8 | 20.1 | 34.0 | 7.0 | 3.3 | 76.8 | 80 | −10 | 82.0 |
| 2-9 | 20.1 | 34.0 | 3.5 | 1.6 | 82.0 | 85 | 10 | 67.2 |
| 2-10 | 20.1 | 34.0 | 49.0 | 6.6 | 76.8 | 80 | 10 | 60.2 |
| 2-11 | 20.1 | 34.0 | 7.0 | 3.3 | 54.8 | 80 | 10 | 53.8 |
| 2-12 | 20.1 | 34.0 | 7.0 | 3.3 | 76.8 | 30 | 10 | 25.0 |
| 2-13 | 20.1 | 34.0 | 7.0 | 3.3 | 76.8 | 160 | 10 | 42.0 |
| 2-14 | 20.1 | 34.0 | 7.0 | 3.3 | 76.8 | 80 | 60 | 42.8 |

EXAMPLE 3

Following the same procedure as in Experiment 1 of Example 1, a reaction and operation were carried out except that 0.32 g of the first added copper powder was replaced with 0.56 g of an iron powder, that 0.20 g of the secondly added copper was replaced with 0.17 g of the iron powder, and that the cooling temperature was −10° C., thereby obtaining p-hydroxybenzoic acid in a total yield of 50%.

EXAMPLE 4

Following the same procedure as in Experiment 1 of Example 1, a reaction was performed except that 0.32 g of the first added copper powder was replaced with 0.60 g of a Raney nickel, that 0.20 g of the secondly added copper was replaced with 0.38 g of the Raney nickel, and that the cooling temperature was −10° C., thereby obtaining p-hydroxybenzoic acid in a total yield of 50%.

What is claimed is:

1. A method for preparing solid p-disodium hydroxybenzoate benzoate which is characterized by comprising the steps of reacting phenol, carbon tetrachloride in an amount of 0.9 to 1.2 moles per mole of phenol and sodium hydroxide in an amount of 7 to 20 moles per mole of phenol prior to the reaction in an aqueous liquid containing 10 to 40% by weight of p-disodium hydroxybenzoate and/or sodium chloride in the presence of a transition metal powder in an amount of 0.01 to 1.00% by weight based on the weight of a reaction system at a reaction temperature of 50° to 150° C.; cooling the resulting reaction mixture to a level of −20° to +20° C.; and separating said solid p-disodium hydroxybenzoate therefrom.

2. A method for preparing solid p-disodium hydroxybenzoate according to claim 1 wherein a transition metal for said transition metal powder is selected from the group consisting of copper, iron, reduced iron, Raney iron, Raney nickel, Raney cobalt, zinc, tin, cadmium and alloys thereof.

3. A method for preparing solid p-disodium hydroxybenzoate according to claim 1 wherein said transition metal powder is a copper powder.

4. A method for preparing solid p-disodium hydroxybenzoate according to claim 1 in which the reaction temperature is 70° to 140° C.

5. A method for preparing solid p-disodium hydroxybenzoate according to claim 4 in which the concentration of the phenol in the aqueous liquid is 5 to 50 weight % and in which the transition metal for said transition metal powder is selected from the group consisting of copper, iron, reduced iron, Raney iron, Raney nickel, Raney cobalt, zinc, tinc, cadmium and alloys thereof.

6. A method for preparing solid p-disodium hydroxybenzoate according to claim 5 in which the reaction is carried out in the presence of 0.1 to 5% by weight based on the weight of the aqueous solution of a non-ionic surface active agent.

7. A method for preparing solid p-disodium hydroxybenzoate according to claim 6 in which the separated solid p-disodium hydroxy benzoate is subjected to an extraction or recrystallization with an alcohol or polar organic solvent.

8. A method for preparing solid p-disodium hydroxybenzosate according to claim 7 in which the phenol concentration is 10 to 40% by weight, the amount of non-ionic surface active agent is 0.5 to 3% by weight and the transition metal is copper.

9. A method for preparing solid p-disodium hydroxybenzoate according to claim 1 in which the reaction is carried out in the additional presence of 0.1 to 5% by weight of the aqueous solution of a non-ionic surface active agent.

10. A method for preparing solid p-disodium hydroxybenzoate according to claim 10 in which the amount of non-ionic surface active agent is 0.5 to 3% by weight.

11. A method for preparing solid p-disodium hydroxybenzoate according to claim 1 in which the separated solid p-disodium hydroxy benzoate is subjected to an extraction or recrystallization from an alcohol or polar organic solvent.

* * * * *